(12) United States Patent
Rockway

(10) Patent No.: US 7,666,447 B2
(45) Date of Patent: *Feb. 23, 2010

(54) COMPOSITIONS INCLUDING KRILL EXTRACTS AND CONJUGATED LINOLEIC ACID AND METHODS OF USING SAME

(75) Inventor: Susie Rockway, Grayslake, IL (US)

(73) Assignee: Pharmanutrients, Gurnee, IL (US)

( * ) Notice: Subject to any disclaimer, the term of this patent is extended or adjusted under 35 U.S.C. 154(b) by 142 days.

This patent is subject to a terminal disclaimer.

(21) Appl. No.: 10/961,578

(22) Filed: Oct. 8, 2004

(65) Prior Publication Data

US 2006/0078625 A1    Apr. 13, 2006

(51) Int. Cl.
*A61K 35/12* (2006.01)
*A61K 35/64* (2006.01)
*A61K 45/00* (2006.01)

(52) U.S. Cl. .................. 424/538; 424/283.1; 424/520
(58) Field of Classification Search ............... None
See application file for complete search history.

(56) References Cited

U.S. PATENT DOCUMENTS 5,986,116 A    11/1999   Iwata et al.
6,265,450 B1 *  7/2001   Asami et al. .............. 514/691
6,800,299 B1 * 10/2004   Beaudoin et al. ........... 424/522
7,208,522 B1 *  4/2007   Menard et al. ............. 514/560

FOREIGN PATENT DOCUMENTS

| | | |
|---|---|---|
| WO | WO 02/09691 | 2/2002 |
| WO | WO 02/09692 | 2/2002 |
| WO | WO 02/09693 | 2/2002 |
| WO | WO 02/09725 | 2/2002 |
| WO | WO 02/102394 | 12/2002 |

* cited by examiner

*Primary Examiner*—David M. Naff
*Assistant Examiner*—Deborah K. Ware
(74) *Attorney, Agent, or Firm*—K&L Gates LLP

(57) ABSTRACT

Methods and compositions for the prevention, therapy and/or treatment of several disease states. The methods comprise the administration of a therapeutically effective amount of a composition including krill extract and conjugated linoleic acid. In addition, the present invention provides new and improved therapeutic compositions including krill extracts and conjugated linoleic acid.

8 Claims, No Drawings

COMPOSITIONS INCLUDING KRILL EXTRACTS AND CONJUGATED LINOLEIC ACID AND METHODS OF USING SAME

PRIORITY CLAIM

This application claims the benefit of U.S. Provisional Patent Application No. 60/309,456, filed Aug. 8, 2001, the disclosures of which are hereby incorporated by reference.

BACKGROUND OF THE INVENTION

This invention generally relates to compositions and methods for preventing and/or treating diseases.

PCT Patent Application No. PCT/CA02/00843 published on Dec. 27, 2002 and entitled "Krill and/or Marine Extracts for Prevention and/or Treatment of Cardiovascular Diseases, Arthritis, Skin Cancer, Diabetes, Premenstrual Syndrome and Transdermal Transport" (the disclosure of which is incorporated herein by reference) discloses krill and/or marine extracts.

Krill is the common name for small, shrimp-like crustaceans, however not shrimp, that swarm in dense shoals, especially in Antarctic waters. It is one of the most important food source for fish, some kind of birds and especially for baleen whales as being an important source of protein. Krill is also a good source of Omega-3 fatty acids, which are well known for their health benefits.

The PCT application states that it is known in the art to use krill and/or marine enzymes for the treatment of a great variety of diseases in human and animals such as infections, inflammations, cancers, HIV/AIDS, pain, polyps, warts, hemorrhoids, plaque, wrinkles, thin hairs, allergic itch, antiadhesion, eye disease, acne, cystic fibrosis and immune disorders including autoimmune disease and cancer.

It is also stated to be known in the art that krill and/or marine oil may be used for the treatment of autoimmune murine lupus and other autoimmune diseases and can also be used for treating cardiovascular diseases.

However, it is stated that the krill and/or marine oil used for these treatments has only conserved its Omega-3 fatty acids as active ingredients, which is a very small part of all the active ingredients of the krill and/or marine itself. This fact reduces the potential of the krill and/or marine oil as a treatment for these diseases.

There is an increasing demand for treatments using products derived from a natural source, therefore, it would be highly desirable to be provided with a krill and/or marine extract having an enhanced potential for prevention and/or treatment and/or management of disease. It is known to use conjugated linoleic acid for the treatment of diseases.

Published PCT Patent Application Nos. PCT/US00/21050, PCT/US00/21047, PCT/US00/21046, and PCT/US00/21044, entitled "Method and Compositions for Preventing and/or Treatment of Diabetes and Glucose Modulation", "Methods and Compositions for Attenuation and/or Prevention of Stress/Catabolic Responses", "Methods and Compositions for the Prevention and Treatment of Inflammation, Osteoarthritis, and Other Degenerative Joint Diseases", and "Methods and Compositions for the Prevention and Treatment of Syndrome X", respectively, (the disclosures of all of which are incorporated by reference) relate to the use of conjugated linoleic acid. As disclosed therein, conjugated linoleic acid has been used for the treatment of disease states.

SUMMARY OF THE INVENTION

In accordance with the present invention there are provided methods of prevention, therapy and/or treatment of several disease states. The methods comprise the administration of a therapeutically effective amount of a composition including krill extract and conjugated linoleic acid with or without other active or inactive ingredients. In addition, the present invention provides new and improved therapeutic compositions including krill extracts and conjugated linoleic acid.

To this end, in an embodiment, the present invention provides a method for preventing the onset of a disease state in an individual comprising the step of administering a therapeutically effective amount of a composition including krill extract and conjugated linoleic acid.

In an embodiment, approximately 1.0 mg to about 15 g per day of krill extract and conjugated linoleic acid are administered.

In an embodiment, the individual is at risk of a disease or ailment chosen from the group consisting of joint ailment, PMS, Syndrome X, cardiovascular disease, bone disease, immune deficiency, diabetes, stress related disease, and hormonal disease.

In an embodiment, the conjugated linoleic acid is chosen from the group consisting of a pure isomer of octadecadienoic acid and a mixture of octadecadienoic acid isomers including: cis-8, cis-10; cis-8, trans-10; trans-8, cis-10; trans-8, trans-10; cis-9, cis-11; cis-9, trans-11; trans-9, cis-11; trans-9, trans-11; cis-10, cis-12; cis-9, trans-12; trans-9, cis-12; trans-10, trans-12; cis-11, cis-13; cis-11, trans-13; trans-11, cis-13; trans-11, trans-13 octadecadienoic acid; 18:3 cis-6, cis-9, trans-11; 18:3 cis-6, trans-10, cis-12; 18:3 cis-8, trans-12, cis-14; 20:3 cis-8, cis-11, trans-13; 20:4 cis-5, cis-8, cis-11, trans-13; 20:4 cis-5, cis-8, trans-12, cis-14; metabolites thereof; and precursors and derivatives thereof.

In an embodiment, the composition includes a flavor.

In an embodiment, the composition includes an artificial sweetener.

In another embodiment of the present invention, a composition for treating a disease state or reducing the risk of a disease state in a patient is provided comprising an effective amount of krill oil in association with conjugated linoleic acid and a pharmaceutically acceptable carrier, wherein said krill oil is obtained from a process comprising the steps of: placing krill and/or marine material in a ketone solvent, preferably acetone to achieve extraction of the soluble lipid fraction from the marine and/or aquatic animal material; separating the liquid and solid contents; recovering a first lipid rich fraction from the liquid contents by evaporation of the solvent present in the liquid contents; placing said solid contents in an organic solvent selected from the group of solvents consisting of alcohol, preferably ethanol, isopropanol or t-butanol and esters of acetic acid, preferably ethyl acetate to achieve extraction of the remaining soluble lipid fraction from said marine and/or aquatic animal material; separating the liquid and solid contents; recovering a second lipid rich fraction by evaporation of the solvent from the liquid contents; and recovering the solid contents.

In yet another embodiment of the present invention, a therapeutic composition is provided comprising an effective amount of krill oil and conjugated linoleic acid in association with a pharmaceutically acceptable carrier, wherein said krill oil comprises Eicosapentanoic acid, Docosahexanoic acid, Phosphatidylcholine, Phosphatidylinositol, Phosphatidylserine, Phosphatidylethanolamine, Sphingomyelin, α-tocopherol, Astaxanthin, and flavonoid.

Still further, the present invention provides a method of treating a disease state comprising the steps of administering a therapeutically effective amount of a composition including conjugated linoleic acid and a krill extract.

In an embodiment, the individual suffers from a disease or ailment chosen from the group consisting of joint ailment, PMS, Syndrome X, cardiovascular disease, bone disease, immune deficiency, diabetes, stress related disease, and hormonal disease.

In a further embodiment of the present invention, a method of producing a therapeutic composition is provided comprising preparing a krill extract obtained from a process comprising the steps of: placing krill and/or marine material in a ketone solvent, preferably acetone to achieve extraction of the soluble lipid fraction from the marine and/or aquatic animal material; separating the liquid and solid contents; recovering a first lipid rich fraction from the liquid contents by evaporation of the solvent present in the liquid contents; placing the solid contents in an organic solvent selected from the group of solvents consisting of alcohol, preferably ethanol, isopropanol or t-butanol and esters of acetic acid, preferably ethyl acetate to achieve extraction of the remaining soluble lipid fraction from the marine and/or aquatic material; separating the liquid and solid contents; recovering a second lipid rich fraction by evaporation of the solvent from the liquid contents; recovering the solid contents; and adding the solid contents to a conjugated linoleic acid containing composition.

Additional features and advantages of the present invention are described in, and will be apparent from, the following Detailed Description of the Invention.

DETAILED DESCRIPTION OF THE INVENTION

In accordance with the present invention, there is provided therapeutic compositions comprising krill extract and conjugated linoleic acid for the prevention and/or treatment and/or therapy of diseases. A variety of treatments and compositions are possible pursuant to the present invention. The compositions can also be used prophylactically to prevent the onset of diseases as well as to maintain a healthy individual.

It is believed that there are synergistic effects achieved by combining conjugated linoleic acid and krill oil extract in a single composition or treatment. These benefits are derived from the two oils that have different compositions but produce enhanced or synergistic benefits through shared eicosanoid mechanisms. These mechanisms include changing membrane composition through phospholipid incorporation, longer chain fatty acid incorporation and conjugated linoleic acid incorporation. In addition to these synergistic shared mechanisms the ability of conjugated linoleic acid to activate peroxisome peroxidation activation receptors (PPAR), which are thought to be involved with glucose and lipid metabolism as well as adipocyte apoptosis produces a synergistic effect. These combined oils are believed to be beneficial in indications, applications and compositions listed below.

Various combinations of the oils can be used. The oils can be topically applied or, parenterally and/or orally delivered. By way of example, a daily dosage can provide as little as 1 mg of the oils or as much as 15 g of the oils; in an embodiment, between 100 mg to 12 g of oil is provided daily. Efficacious doses will depend on the condition being addressed. By way of example, combinations of either oil can be used in a 1:1 ratio or a ratio of 0.05:1 to 1:0.05. These oils can be combined with other organic or inorganic compounds known to further enhance the conditions being addressed.

With respect to the krill extract, a multi-therapeutic oil extract free of enzyme is derived from krill and/or marine, found in any marine environment around the world, for example, the Antarctic ocean (euphasia superba), the Pacific ocean (euphasia pacifica), the Atlantic ocean, the Indian ocean, in particular coastal regions of Mauritius Island and/or Reunion Island of Madagascar, Canadian West Coast, Japanese Coast, St-Lawrence Gulf and Fundy Bay, and this oil extract is a free fatty acid lipid fraction.

The extraction process can be described as the following:

(a) placing marine and/or aquatic krill and/or marine in a ketone solvent, preferably acetone, to achieve the extraction of grease from the krill and/or marine;

(b) separating the liquid and the solid phases;

(c) recovering a lipid rich fraction from the liquid phase obtained at step (b) by evaporation of the solvent present in the liquid phase;

(d) placing the solid phase in an organic solvent, which can be alcohol, preferably ethanol, isopropanol or t-butanol, or esters of acetic acid, preferably ethyl acetate. This in order to extract the remaining soluble lipid fraction from the solid phase;

(e) separating the liquid and the solid phases; and (f) recovering a lipid rich fraction from the liquid phase obtained at step (e) by evaporation of the solvent present in the liquid phase.

As set forth in PCT Application No. PCT/CA02/00843, the active components of the enzyme-free krill and/or marine oil extract are:

Lipids
i) Omega-3:
i. Eicosapentanoic acid: 8 g/100 g
ii. Docosahexanoic acid: 2 g/100 g
iii. Linoleic acid: 0.10 g/100 g
iv. Alpha-linolenic acid: >0.3 g/100 g The PCT application states that in the preferred embodiment, the Omega-3 fatty acids are found in more than 30 g/100 g ii) Omega-6:
i. Linoleic acid: >0.9 g/100 g
ii. Arachidonic acid: <0.45 g/100 g, preferably <0.6 g/100 g iii) Omega-9:
i. Oleic acid: >5 g/100 g
iv) palmitic acid: >10 g/100 g
v) palmitoleic acid: 0.08 g/100 g
vi) stearic acid: >0.5 g/100 g Phospholipids
Phosphatidylcholine: >4.5 g/100 g
Phosphatidylinositol: >107 mg/100 g
Phosphatidylserine: >75 mg/100 g
Phoshatidylethanolamine: >0.5 g/100 g
Sphingomyelin: >107 mg/100 g Neutral lipids
Cholesterol: <3 g/100 g
Triglycerides: <55 g/100 g
Monoglycerides: >0.5 g/100 g As set forth in the PCT application, the neutral lipids of the krill and/or marine extract also comprises:

Diglycerides: >0.5 g/100 g
Antioxydants
A-tocopherol (vitamin E): >1.0 IU/100 g
All-trans retinol (vitamin A): >1500 IU/100 g
B-carotene: >3000 μg/100 ml
Pigments Astaxanthin: >20 mg/100 g
Canthaxanthin: >2 mg/100 g
Metals
Zinc: >0.1 mg/100 g
Selenium: >0.1 mg/100 g The PCT application states in another embodiment, the krill and/or marine extract also comprises:
Flavonoids: >0.5 mg/100 g
Sodium: <500 mg/100 g
Calcium: >0.1 mg/100 g
Potassium: >50 mg/100 g
Aluminum: <8.5 mg/100 g
Protein: >4 g/100 g
Moisture and volatile matter: <0.8%

The PCT application sets forth that after characterization of the krill and/or marine oil extract, it was determined that the extract contains less than 25 ppm of solvent residue from the extraction process.

The oil has the following stability indexes:
Peroxide value: <0.1 (mEq/kg)
Oil Stability index: <0.1 after 50 hours at 97.8° C.
Saponification index: 7-180
Iodine value: 60-130%

Pursuant to the present invention, the method and composition comprises administering krill extract and conjugated linoleic acid. If desired, the composition can include non-active ingredients and/or agents such as flavors, artificial sweeteners, excipients, etc. The product of the present invention is intended to provide a physiologically based means to aid in maintaining normal physiological homeostasis.

Conjugated linoleic acid refers to a group of dienoic derivatives of linoleic acid that occur naturally in milk and meat of ruminating animals. It can be synthesized in the laboratory and in commercial scale and is currently available commercially as a dietary supplement.

Conjugated linoleic acid is believed to be absorbed efficiently into the body in a manner similar to that of other fatty acids, e.g., linoleic acid. The safety of conjugated linoleic acid has been demonstrated in detailed toxicological assessments and through extensive use in humans, both as a naturally occurring substance and as a dietary supplement. It is believed that conjugated linoleic acid is safe for human consumption.

Pursuant to the present invention, the conjugated linoleic acid can be conjugated linoleic acid such as that set forth in U.S. Pat. No. 5,986,116 the disclosure of which is incorporated herein by reference.

In an embodiment, the conjugated linoleic acid is either a pure isomer of octadecadienoic acid, or a mixture of octadecadienoic acid isomers selected from the group consisting of: cis-8, cis-10; cis-8, trans-10; trans-8, cis-10; trans-8, trans-10; cis-9, cis-11; cis-9, trans-11; trans-9, cis-11; trans-9, trans-11; cis-10, cis-12; cis-9, trans-12; trans-9, cis-12; trans-10, trans-12; cis-11, cis-13; cis-11, trans-13; trans-11, cis-13; trans-11, trans-13 octadecadienoic acid; metabolites thereof, including but not limited to 18:3 cis-6, cis-9, trans-11; 18:3 cis-6, trans-10, cis-12; 18:3 cis-8, trans-12, cis-14; 20:3 cis-8, cis-11, trans-13; 20:4 cis-5, cis-8, cis-11, trans-13; 20:4 cis-5, cis-8, trans-12, cis-14; as well as precursors or derivatives thereof.

Pursuant to the present invention, the composition can be taken as a dietary supplement or a pharmacological product.

By way of example and not limitation, contemplative examples of indications/applications that can be treated benefit from the present invention are as follows:

INDICATIONS/APPLICATIONS

1. Joint
2. PMS
3. Syndrome X
4. Body Composition
5. Cardiovascular
6. Bone Content (Health)
7. Immune enhancement
8. Diabetes
9. Anticarcinogen
10. Hormonal Fluctuations
11. Quality of Life-feel good
12. Stress Catabolic Response
13. Skin, hair and nails
14. Anti-inflammatory
15. Antioxidant 1. Joint Anti-inflammatory reactions: Both conjugated linoleic acid and krill oil reduce the adverse effects that occur when the eicosanoid pathway through COX-1 and COX-2 enzymatic reactions leading to prostaglandin synthesis, such as PGE-2, PGE-1, leukotrienes and thromboxanes, are extended beyond normal, physiological needs from those signals initially produced by stress or injury. The continuation of eicosanoid production leads to chronic inflammation as indicated in osteoarthritis, joint pain, cartilage breakdown, increased adipose deposition, bone breakdown. In addition, involvement of those eicosanoids (proinflammatory) known to increase platelet aggregation and eventual plaque formation when endothelial injury has occurred—all involved with cardiovascular disease.

2. PMS

The most probable cause of the physical symptoms of PMS seems to be the combined interaction of hormones and essential nutrients leading to an increased inflammatory response.

The emotional symptoms of PMS seem to be propagated by an exaggerated response of neurotransmitters to psychosocial stresses. Reducing arachidonic incorporation or its release from phospholipids (SN-2 position) decreases formation of prostaglandin E2 which when elevated continues inflammatory response. By increasing the ratio of Omega-3 fatty acids to Omega-6 (as in the case of krill oil): and by reducing the synthesis of arachidonic acid (by decreasing linoleic acid, its precursor) (both conjugated linoleic acid and krill oil accomplish this by two different mechanisms) will lead to reduced inflammatory responses.

3. Syndrome X

Metabolic syndrome encompasses specific abnormalities such as elevated plasma TG's, low levels of HDL, increased blood pressure, fasting glucose and increased abdominal adipose tissue. Having three or more of these conditions constitutes Syndrome X. Conjugated linoleic acid decreases elevated glucose levels, decrease elevated TG levels and decrease high blood pressure. Krill oil lowers elevated glucose and reduce plasma cholesterol, TG and simultaneously elevate HDL levels. The combination of these two oils should have a positive impact on those specific parameters involved with this syndrome.

4. Body Composition

Conjugated linoleic acid reduces fat accumulation in humans by decreasing lipoprotein lipase (LPL) synthesis, hormone lipase synthesis, decrease adipose cell number by apopotosis at early cell development, and increase fat as a fuel source (beta-oxidation). In addition, conjugated linoleic acid increases muscle mass (LBM) even under catabolic conditions such as calorie reduction via weight loss. Krill increases energy level, feelings of wellness and energy levels, skin, hair and nails improvement, which combined with fat loss will give physical and emotional benefits in those using these oils.

5. Cardiovascular Health

Cardiovascular health can be improved via the present invention due to the ability of the compositions to achieve the following:

LDL cholesterol lowering (conjugated linoleic acid, krill oil)

HDL elevation or maintenance (krill oil)

TG lowering (conjugated linoleic acid and krill oil)

Reducing elevated glucose (conjugated linoleic acid and krill oil)

Reducing abdominal adipose (conjugated linoleic acid)

Increasing elasticity of endothelial lining and reducing platelet aggregation precursors (anti-inflammatory response) (conjugated linoleic acid and krill oil)

6. Bone Health

Reducing the chronic stress catabolic response and inflammatory response by intake of both conjugated linoleic acid and krill oil should dramatically favor an environment of bone synthesis and reduce bone degradation. The Omega-3 present in krill oil improves the ability of conjugated linoleic acid to increase bone mineral content possibly by conjugated linoleic acid's ability to decrease inflammatory prostaglandins. Krill oil also contains other compounds such as antioxidants and flavonoids that would likely improve the micro-environment surrounding bone cells and joints.

7. Immune Enhancement

Conjugated linoleic acid increases antibody response to viral invasion. Combined with the antioxidants, Omega-3, vitamin and mineral profile and phospholipids present in krill oil, enhancing macrophage ability to respond to immune challenge.

8. Diabetes

Conjugated linoleic acid decreases elevated glucose and increase insulin sensitivity. Krill oil decreases elevated glucose; combining these oils will strengthen their ability to promote glucose utilization and favor a healthier glucose plasma level.

9. Anticarcinogen

Conjugated linoleic acid is a naturally occurring anticarcinogen. Krill oil protects against free radical damage from sunlight and environmental toxins. Both oils will have a favorable impact in reducing risk of cancer, especially those cancers induced by free radical damage.

10. Hormonal Fluctuations

Significant improvement in female mood swings occur prior and during menstruation. This suggests that there will likely be overall benefit in reducing hormonal changes that naturally occur during each month by increasing the Omega-3 portion of triglycerides and phospholipids that are part of brain cells. Increasing membrane fluidity by increasing long chain fatty acids (Omega-3) enhances the ability of protein receptors to respond to substrate interaction and therefore, should be improved general cell health by the addition of krill oil and conjugated linoleic acid.

In addition, cell membrane composition will be improved by the naturally occurring phospholipids existing in krill oil. The unique chemical composition appears to allow the molecule to be absorbed quickly and is easily incorporated into cell membranes, which could explain the neurological and hormonal aspects of the observed benefits seen in women taking this product. The existence of these unique phospholipids with a phosphate group in SN-2 position, allows greater effects of conjugated linoleic acid to act as a COX-2 inhibitor since the conjugated linoleic acid molecule would not have to be released by phospho lipases within the cell, thus more conjugated linoleic acid will exist in the free form and more should be available for either PPAR activation or further synthesis of conjugated linoleic acid elongated and desaturated products. Therefore, the combination of the two oils will have an enhanced and perhaps synergistic responses in reducing the ill effects of inflammatory eicosanoids, as well as increasing the fluidity of cell membranes.

11. Quality of Life—Enhanced Wellness

Subjective data from clinical study supports the overall feelings of increased mental focus, more energy, less fatigue and less mood swings.

12. Stress Catabolic Response

The anti-inflammatory response of both conjugated linoleic acid and krill oil will reduce stress catabolic response (hormonally induced reaction to stressors in life) and will enhance the bodies ability to maintain homeostasis.

13. Skin, Hair and Nails

Krill oil improves women's perception of healthier skin, hair and nails, which is likely do to the improved ratio of Omega-3 to Omega-6 fatty acids in addition to the antioxidant properties of Vitamin A and Vitamin B, flavonoids and astathanxine. Conjugated linoleic acid may also help these factors by displacing arachidonic acid and allowing more Omega-3 to compete with COX enzymes and increase odd numbered eicosanoids.

14. Anti-Inflammatory

Aging and many chronic diseases in humans is related indirectly if not directly to the ability of cells to reduce chronic inflammatory responses. Thus, conditions such as asthma, rheumatoid arthritis, allergies, etc. could all possibly be improved by reducing the eicosanoids responsible for the continuation of inflammation and the cytokines involved in perpetuating those chronic disorders. Both conjugated linoleic acid and krill oil are shown to reduce these inflammatory compounds.

15. Antioxidant

Conjugated linoleic acid behaves as a weak antioxidant. Krill oil is a potent anti-oxidant. Thus, both oils will have a beneficial impact in cell's ability to reduce free-radical damage associated with cell death, aging, neurological damage, and cardiovascular disease by specific reduction in LDL oxidation.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the claims.

The invention is claimed as follows:

1. A method for treating an individual having a disease state selected from the group consisting of a joint ailment, PMS, Syndrome X, cardiovascular disease, bone disease and diabetes, the method comprising administering to the individual a therapeutically effective amount of a composition including conjugated linoleic acid and a krill extract comprising krill oil.

2. The method of claim 1 wherein about 1 mg to about 15,000 mg per day of krill extract and conjugated linoleic acid are administered.

3. The method of claim 1 wherein the conjugated linoleic acid is chosen from the group consisting of a pure isomer of octadecadienoic acid and a mixture of octadecadienoic acid isomers selected from the group consisting of: cis-8, cis-10; cis-8, trans-10; trans-8, cis-10; trans-8, trans-10; cis-9, cis-11; cis-9, trans-11; trans-9, cis-11; trans-9, trans-11; cis-10, cis-12; cis-9, trans-12; trans-9, cis-12; trans-10, trans-12; cis-11, cis-13; cis-11, trans-13; trans-11, cis-13; trans-11, trans-13 octadecadienoic acid; 18:3 cis-6, cis-9, trans-11; 18:3 cis-6, trans-10, cis-12; 18:3 cis-8, trans-12, cis-14; 20:3 cis-8, cis-11, trans-13; 20:4 cis-5, cis-8, cis-11, trans-13; 20:4 cis-5, cis-8, trans-12, cis-14 and combinations thereof.

4. The method of claim 1 wherein the composition includes a flavor.

5. The method of claim 1 wherein the composition includes an artificial sweetener.

6. The method of claim 1 wherein the krill extract and conjugated linoleic acid are present at a ratio of 0.05:1 to 1:0.05.

7. The method of claim 1 wherein the composition includes excipients.

8. The method of claim 1 wherein approximately 100 mg to about 12,000 mg per day of krill extract and conjugated linoleic acid are administered.

* * * * *